United States Patent [19]
Kubo

[11] Patent Number: 6,142,976
[45] Date of Patent: Nov. 7, 2000

[54] PREFILLED SYRINGE

[75] Inventor: Tomohiko Kubo, Kusatsu, Japan

[73] Assignee: Nissho Corporation, Osaka-fu, Japan

[21] Appl. No.: 08/987,052

[22] Filed: Dec. 9, 1997

[30] Foreign Application Priority Data

Dec. 13, 1996 [JP] Japan .................................. 8-333406

[51] Int. Cl.[7] .................................................. A61M 5/32
[52] U.S. Cl. .......................... 604/199; 604/187; 604/218; 604/221
[58] Field of Search ................................ 604/240, 187, 604/199, 212, 218, 221, 231

[56] References Cited

U.S. PATENT DOCUMENTS

| | | |
|---|---|---|
| 2,888,924 | 6/1959 | Dunmire . |
| 3,754,644 | 8/1973 | Hompel ................................ 604/199 |
| 4,713,060 | 12/1987 | Rivli ..................................... 604/199 |
| 5,027,233 | 10/1998 | Futagawa et al. ..................... 604/232 |
| 5,702,015 | 7/1998 | Yanai et al. ........................... 604/218 |

FOREIGN PATENT DOCUMENTS

| | | |
|---|---|---|
| 1555711 | 1/1969 | France . |
| 5532605 | 8/1980 | Japan . |
| 534669 | 9/1993 | Japan . |
| 1041311 | 9/1966 | United Kingdom . |

*Primary Examiner*—Corrine McDermott
*Assistant Examiner*—Kent Gring
*Attorney, Agent, or Firm*—Birch, Stewart, Kolasch & Birch, LLP

[57] ABSTRACT

A prefilled syringe including a barrel having an opening at opposite ends and an inwardly projecting annular wall at a distal end and a plastic film tube hermetically bonded to a needle-connecting member and the plunger at each end.

7 Claims, 2 Drawing Sheets

PREFILLED SYRINGE

BACKGROUND OF INVENTION

1. Field of the Invention

The present invention relates to a prefilled syringe and, more particularly, to a pre-filled syringe having a non-gasket structure requiring no lubricant such as silicone oil, which is substantially free from eluting material and low in sliding resistance between a syringe barrel and a plunger.

2. Description of the Prior Art

There have been known so-called prefilled syringes or a syringe ready for administration of a liquid medicine to a patient, comprising a barrel previously filled with a liquid medicine. The administration can be done with such a syringe by removing a hermetic seal from a tip of the barrel and then fitting a hypodermic needle over the tip of the barrel. The barrel filled with a liquid medicine is generally sealed at one end by a rubber gasket and at the other end or a needle-connecting portion by a rubber plate.

However, such prefilled syringes of the prior art employing such sealing members have a serious problem for use in infusion since the rubber plate and rubber gasket allow compounding agents such as sulfur and vulcanization accelerators or impurities contained therein to elute in the liquid medicine during storage of the syringes.

In order to overcome such disadvantages of the prefilled syringe of the prior art, in examined Japanese Utility model publication No. 55-32602 it has been proposed to use a prefilled syringe comprising a barrel of glass in combination with sealing member coated or covered with a thin film of a plastic material other than fluorine-contained resin at all the surfaces to be in contact with a liquid medicine. However, such a syringe has a problem in slidability of the resin coated sealing members. This problem may be overcome by use of gaskets made of fluorine contained resin, but fluorine contained resin causes other problems; for example in liquid-tightness and airtightness when the resin coated sealing members are used in combination with the glass barrels.

For these reasons, disposable syringes widely used today are those employing a barrel made of plastics. When using the plastic barrels in combination with a gasket made of plastics other than fluorine-contained resin, it is necessary to apply silicone oil as a lubricant on sliding surfaces of the gasket since the slidability of the gasket decreases with increase in liquid-tightness and airtightness between the gasket and barrel. However, silicone oil is a foreign substance for the medicament to be administered and causes particulate contamination of the medicament.

To solve such problems, it has been proposed in examined Japanese utility model publication No. 5-34669 to use a gasket of which all the surfaces to be in contact with a liquid medicine and to be slid on the inner wall of the barrel are covered with a thin film selected from the group consisting of polytetrafluoroethylene film, ethylene-tetra fluoroethylene copolymer film and ultra-high-molecular weight polyethylene film and which has a length of a contacting surface between a peripheral portion of the gasket and the inner wall of the barrel being limited within a certain range.

Although the gasket disclosed in examined publication No. 5-34669 is sufficient when used for ordinary syringes, they causes problems in liquid-tightness and airtightness when used for prefilled syringes. For example, if the plunger is pressed hardly during storage, the liquid medicine may leak out from the syringe, different from the close contact between the elastic gasket and inner wall of the barrel.

SUMMARY OF THE INVENTION

The present invention has been made to overcome the aforesaid disadvantages in particular to provide a prefilled syringe which is substantially free from contamination of the medicament or from elution of foreign substances, excellent in liquid-tightness and airtightness, and low in sliding resistance between the plunger and barrel in use.

These and other objects of the present invention are solved by employing a flexible plastic film tube previously filled with a liquid medicine and adapted to be squeezed with a plunger to administer the medicament.

According to the present invention, there is provided a prefilled syringe including;

a barrel having an opening at opposite ends and an inwardly projecting annular wall at a distal end a plunger fluid-tightly inserted in a proximal end of the barrel so as to be slidable along the inner wall of the barrel;

a needle-connecting member attached to the annular wall to fluid-tightly close the opening of the annular wall;

a plastic film tube hermetically bonded to the needle-connecting member and the plunger at each end;

said needle-connecting member having at its rear end a skirt portion of an outer diameter equal to an inner diameter of said barrel, said skirt portion being fitted in the distal end of the barrel, said film tube being bonded to the outer wall of the rear side of the skirt portion.

Preferably, the plunger is so formed as to have a head portion with a configuration complementary to that of an inner wall of the skirt portion of the needle-connecting member to improve quantification of injected medicament.

In order to improve the quantitative administration and operatability of the plunger, the plunger may be provided with a packing for providing a right sliding resistance between the inner wall of the barrel and the plunger, at a position adjacent to a bonded position of the film tube. Further, a packing may be arranged between the annular wall of the barrel and the needle-connecting member to prevent leakage of the medicament when a cap has been removed from the syringe.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

These and other objects, features and advantages of the present invention will become apparent from the following detailed description on preferred embodiments thereof with reference to the accompanying drawings which are given by way of illustration only, and thus are not limitative of the present invention, and wherein.

DETAILED DESCRIPTION OF THE PREFERRED EMBODIMENTS

Figure 1:
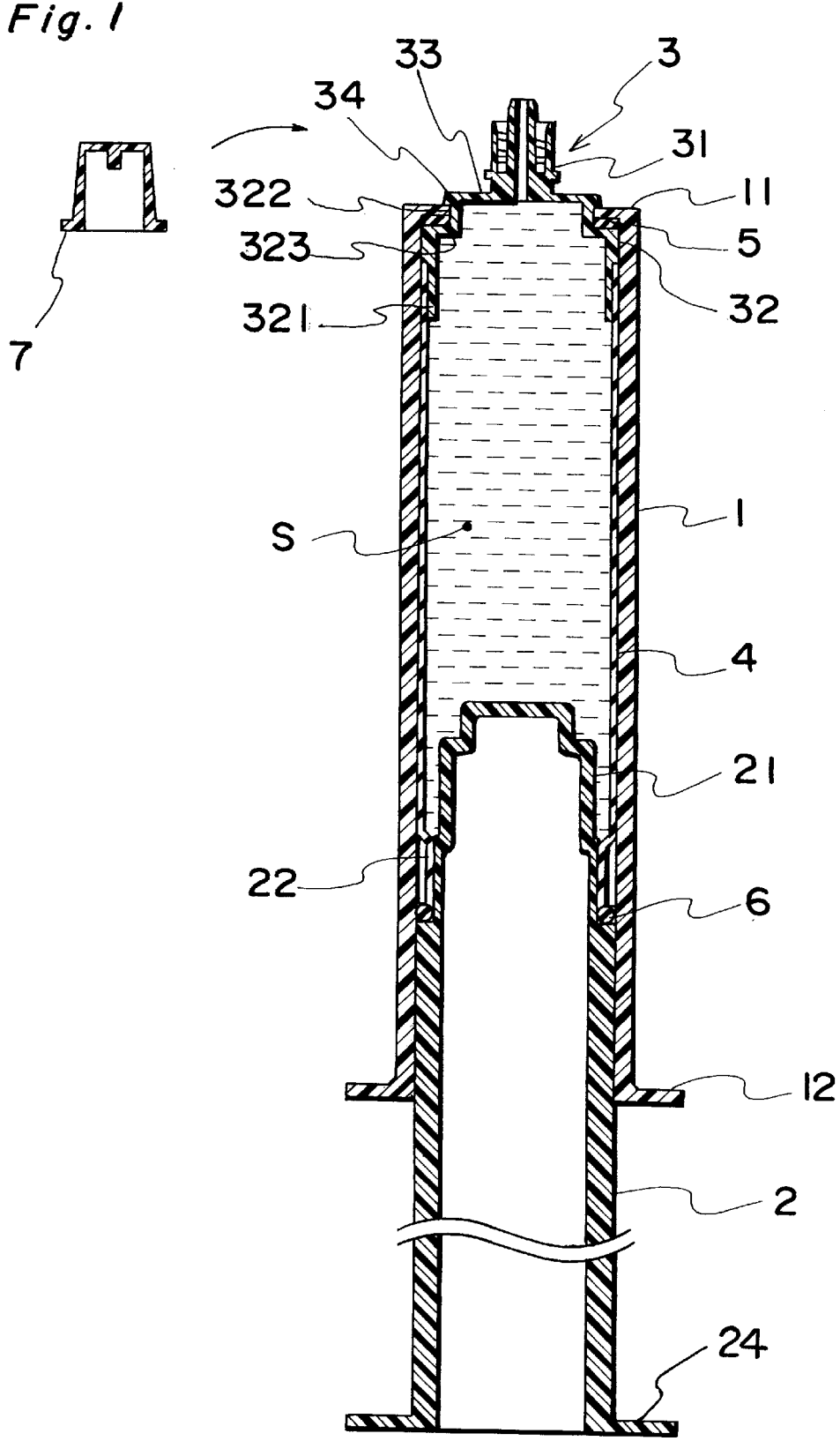
FIG. 1 is a cross-sectional view of a prefilled syringe according to the present invention with a cap being removed.
Figure 2:
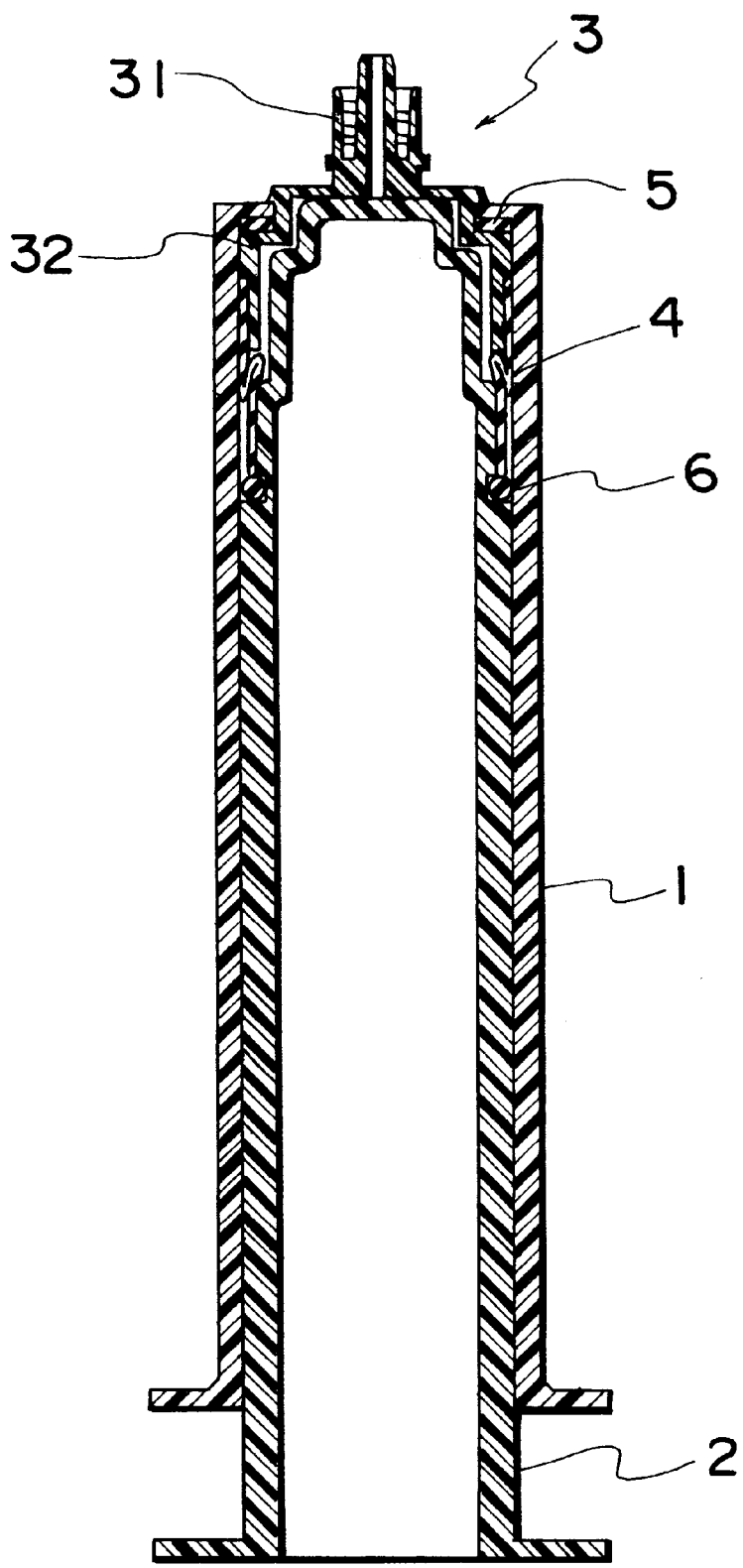
FIG. 2 is a cross-sectional view of the prefilled syringe of FIG. 1, illustrating a plunger being advanced to the distal end of the barrel.

Referring now to FIGS. 1 and 2, there is shown a prefilled syringe according to the present invention, which comprises a barrel 1 having an inwardly projecting annular wall 11 at a distal end, a plunger 2 inserted into the barrel 1 through a proximal end of the barrel 1, a needle-connecting member 3 attached to the annular wall 11 of the barrel 1, and a plastic film tube 4 bonded at one end to the needle-connecting member 3 and at the opposite end to the plunger 2. The needle-connecting member 3 has a skirt portion 32 housed in the barrel 1, and the film tube 4 is bonded to the outer wall of the rear end of the skirt portion 32.

As illustrated in the figures, the prefilled syringe includes a packing 5 arranged between the annular wall 11 of the barrel 1 and the skirt portion 32 of the needle-connecting member 3, and a packing 6 arranged between the inner wall of the barrel 1 and the plunger 2. The packing 6 is fitted on the plunger 2 and located adjacent to the bonded portion of the film tube 4.

The barrel 1 is a cylindrical member provided at a distal end with an inwardly extending wall 11 and at the distal end with a flange 12 for gripping the syringe with fingers. The stopper wall 11 is an annulation for attachment of the needle-connecting member 3 to the barrel 1. The needle-connecting member 3 can be attached to the barrel 1 by inserting the needle-connecting member 3 into a bore of the stopper wall 11 through the proximal open end of the barrel 1 and hermetically fixing it to the distal end of the barrel by press-fitting. A molding material generally used for the barrel 1 is a transparent synthetic resins such as, for example, polypropylene, polyethylene, cyclopolyolefin, polycarbonate, polymethyl-methacrylate, polystyrene, polyvinyl chloride, acrylonitrile-butadiene-styrene copolymer (ABS) or the like.

The plunger 2 is a member of a solid cylinder or a hollow cylinder with a closed-top and is so designed as to have an outer diameter slightly smaller than the inner diameter of the barrel to allow the plunger to move smoothly along the inner wall of the barrel 1. Preferably, the head portion 21 of the plunger 2 is formed into a configuration complementary to that of the inner wall of the needle-connecting member 3. The plunger 2 is provided at a portion adjacent to the head portion 21 with a tube-bonding portion 22 for attachment of the film tube 4 and at a portion adjacent to the bonding portion 22 with a packing 6. Preferably, the packing 6 is fitted on an annular groove formed between the tube-bonding portion 22 and a plunger body 2. The packing 6 provides a suitable sliding resistance between the plunger 2 and the barrel 1, thereby improving the operatability of the plunger 2. At the proximal end the plunger 2 is provided with a flange 24 to make it easy to perform pushing operation. As a material for plunger 2, it is preferred to use a synthetic resin such as polypropylene, polyethylene, polybutylene resin, cyclopolyolefin and the like so that the film tube 4 can be fluid-tightly bonded to the tube-bonding portion 22 of the plunger 2 by thermal bonding or thermal welding.

The needle-connecting member 3 is a cap-shaped member attached to the stopper wall 11 of the barrel 1 to fluid-tightly close the open end of the barrel 1. The needle-connecting member 3 includes a connecting means 31 extending forwardly from a top wall 33, and a skirt portion 32 extending from the top wall 33 in the direction opposite to the connecting means 31. The skirt portion 32 is so formed as to have an outer diameter equal to the inner diameter of the barrel 1. Extending from the rear side of the skirt portion 32 is a tube-bonding portion 321 with an outer diameter smaller than that of the skirt portion 32 for attachment of the film tube 4.

The skirt portion 32 is reduced in diameter at the front portion to form an engaging portion 322 with an outer diameter equal to the diameter of the opening of the stopper wall 11 of the barrel 1. The engaging portion 322 is extended over the opening of the stopper wall 11 of the barrel 1 and terminated at the top wall 33. The top wall 33 is provided at its peripheral portion with an annular under cut rib 34 so that the needle-connecting member 3 can be forced into the opening of the stopper wall 11 of the barrel 1 from the rear side of the barrel 1. The packing 5 is preferably arranged between the stopper wall 11 of the barrel and the skirt portion 32. The engaging portion 322 is so designed as to have a length slightly smaller than the sum of a thickness of the stopper wall 11 and a thickness of the packing 5, thus making it possible to clamp down the stopper wall 11 between the annular rib 34 and the stepped portion 323 of the skirt portion 32 when the needle-connecting member 3 is forcedly fitted in the opening of the stopper wall 11.

The film tube 4 is a tubular film made of a thermoplastic resin such as polypropylene, polyethylene, polybutylene resin, thermoplastic elastomer, ethylene-vinyl acetate copolymer (EVA). This tubular film 4 is bonded at its both ends to the tube-bonding portion 22 of the plunger 2 and tube-bonding portion 321 of the needle-connecting member 3 by thermal bonding. The film tube 4 has an outer diameter equal to the inner diameter of the barrel except for the bonded portion to the plunger 2 and forms a container (hereinafter referred to as a "film tube container") for a liquid medicine S between the top end 21 of the plunger 2 and the skirt portion 32 of the needle-connecting member 3 in cooperation with the plunger 2 and the needle-connecting member 3.

After the film tube container has contained the liquid medicine S, the needle-connecting member 11 is covered with a cap 7 to cover and protect the liquid medicine S in the film tube container. As a molding material for packing 5 and 6, there may be used those such as polyethylene or elastic materials such as butyl rubber, isoprene rubber, thermoplastic elastomer or the like.

EXAMPLE 1

Using polypropylene as a molding material for barrels, and using polyethylene as a molding material for plungers, needle-connecting members and film tubes, there were prepared barrels, plungers, needle-connecting members, film tubes. These parts were assembled to prepare 100 units of prefilled syringes as shown in FIG. 1 with a capacity of 50 ml. Packing of polybutyl chloride were respectively arranged between the barrel and needle-connecting member and between the barrel and plunger. The film tubes were 30 to 200 $\mu$m in thickness and 29.0 mm in inner diameter.

The prefilled syringes were subjected to a sliding test and fine-particle test. The sliding test is carried out by measurement of an initial sliding resistance between the plunger and the barrel by pushing the plunger at a rate 100 mm/min with an Instron type testing machine (Instron 5560 produced by Instron Japan). The fine-particle test is a test for measurement of the number of fine particles with a particle size of not less than 0.5 $\mu$m eluted into the distilled water: Japanese pharmaceutical codex defines that the number of fine particles with a particle size of not less than 0.5 $\mu$m must be not more than 100). Results are listed in Table 1.

EXAMPLE 2

Using the barrels, plungers, needle-connecting members and film tubes prepared in Example 1, there were prepared 100 units of prefilled syringes without use of packing between the barrel and needle-connecting member and between the barrel and plunger. The assembled prefilled syringes were subjected to the sliding test and fine-particle test in the same manner as Example 1. Results are listed in Table 1.

COMPARATIVE EXAMPLE 1

Using polypropylene as a molding material for barrels and plungers and using butyl rubber as a molding material for gaskets, there were prepared barrels, plungers and gaskets for the prefilled syringes of the prior art. These parts were assembled to produce 10 units of prefilled syringes of the prior art with a capacity of 50 ml. The assembled prefilled syringes were subjected to the sliding test and fine-particle test in the same manner as Example 1. Results are listed in Table 1.

TABLE 1

|  | Number of particles above 0.5 μm (particles/ml) | Sliding resistance (kgf) |
| --- | --- | --- |
| Example 1 | 3 | 0.8 |
| Example 2 | — | 0.1 |
| Comparative Ex. 1 | 50 | 1.3 |

As can be seen from the results shown in Table 1, the prefilled syringe according to the present invention is much improved in sliding resistance and lowered in elution of fine particles.

EXAMPLE 3

Using the barrels, plungers, needle-connecting members, film tubes and packing prepared in Example 1, there were prepared 10 units of prefilled syringes having a construction shown in FIG. 1. The prefilled syringes were subjected to a quantitative test for discharge and a leakage test. The quantitative test for discharge is a test for measurement of the ability to conserve the discharged quantity, while the leakage test is a test for measurement of a leaked amount of liquid which may occur when the cap is being removed. The quantitative test for discharge was carried out with a syringe pump at a piston push rate of 150 ml/h. Results are shown in Table 2.

EXAMPLES 4 and 5

Using the barrels, plungers, needle-connecting members, film tubes and packing prepared in Example 1, there were respectively prepared 10 units of prefilled syringes having the same construction as that of FIG. 1 except for the packing between the barrel and plunger being removed (Example 4), and 10 units of prefilled syringes having the same construction as that of FIG. 1 except for the packing between the barrel and needle-connecting member being removed (Example 5). For the prefilled syringes, the quantitative test for discharge and leakage test were carried out in the same manner as Example 3. Results are shown in Table 2.

COMPARATIVE EXAMPLE 2

There were prepared 10 units of prefilled syringes in the same manner as Comparative Example 1. For the resultant prefilled syringes, the quantitative test for discharge and leakage test were carried out in the same manner as Example 3. Results are shown in Table 2.

TABLE 2

|  | Amount of Leakage (ml) | Quantity of discharge (ml/min) |
| --- | --- | --- |
| Example 3 | 0 | 2.46 + 0.03 |
| Example 4 | 0 | 2.16 + 0.10 |
| Example 5 | 0.2 | 2.45 + 0.04 |
| Comp. Ex. 2 | 0 | — |

Note:
Quantity of discharge is calculated from data obtained between 5 to 15 minutes after the beginning of the test.

As can be seen from the results shown in Table 2, the quantitative discharge is affected by the packing between the barrel and the needle-connecting member and the removal of the packing between the barrel and the needle-connecting member causes leakage of the liquid when the cap is removed.

Accordingly, the prefilled syringe according to the present invention provides the following advantages:

(1) Since the prefilled syringe has no gasket which is brought into contact with a liquid medicine and since the liquid medicine is contained in the film tube container, there is no fear of interfusion of any foreign material even if a lubricating oil such as silicone oil is applied on the inner surface of the barrel.

(2) Since the resistance to push the plunger depends on the sliding resistance between the barrel and packing of the plunger, it is possible to inject the liquid medicine with an appropriate strength by suitable selection of the packing to be mounted on the plunger.

(3) It is possible to store the liquid medicine for the long term since the liquid medicine is contained and sealed in the film tube container.

(4) There is no need to perform segregated disposal since prefilled syringe employs no parts made of glass.

(5) The liquid medicine can be administered in completely sterilized conditions as the prefilled syringe is a closed system.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

I claim:

1. A prefilled syringe including;

a barrel having a proximal open end and a distal open end provided with an inwardly projecting annular wall;

a plunger fluid-tightly and slidably arranged in the proximal side of the barrel;

a needle-connecting member attached to the annular wall of the barrel to fluid-tightly close an opening of the annular wall, said needle-connecting member being provided with a skirt portion at a rear end thereof, said skirt portion having an outer diameter equal to an inner diameter of said barrel and being fitted in the distal end of the barrel; and a plastic film tube fitted on and hermetically bonded at one end thereof to the skirt portion of the needle-connecting member and at the opposite end to the plunger to form a container for a liquid medicine.

2. The prefilled syringe according to claim 1, wherein the plunger has a head portion with a configuration complementary to that of an inner wall of the skirt portion of the needle-connecting member.

3. The prefilled syringe according to claim 1, wherein the plunger is provided with a packing for providing a right sliding resistance between the inner wall of the barrel and the plunger, said packing being arranged at a position adjacent to a bonded position of the film tube.

4. The prefilled syringe according to claim 3, wherein said is a packing arranged between the annular wall of the barrel and the needle-connecting member.

5. The prefilled syringe according to claim 3, wherein said plastic film tube is thermally bonded to at least a portion of said plunger and said needle-connecting member.

6. The prefilled syringe according to claim 5, further comprising a tube-bonding portion having an outer diameter smaller than that of said skirt portion, said tube-bonding portion extending from a rear side of said skirt portion.

7. The prefilled syringe according to claim 5, wherein the plastic film tube has an outer diameter equal to the inner diameter of the barrel.

* * * * *